(12) United States Patent
Kunche Babu et al.

(10) Patent No.: US 11,359,149 B2
(45) Date of Patent: Jun. 14, 2022

(54) PROCESS CONFIGURATION FOR PRODUCTION OF PETROCHEMICAL FEED-STOCKS

(71) Applicant: Indian Oil Corporation Limited, Mumbai (IN)

(72) Inventors: Srinivas Kunche Babu, Faridabad (IN); Bhushan Bharat, Faridabad (IN); Vetterkunnel Kumaran Satheesh, Faridabad (IN); Debasis Bhattacharyya, Faridabad (IN); Shailendra Kumar Sharma, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

(21) Appl. No.: 17/236,315

(22) Filed: Apr. 21, 2021

(65) Prior Publication Data

US 2021/0324279 A1    Oct. 21, 2021

(30) Foreign Application Priority Data

Apr. 21, 2020    (IN) .............................. 202021017031

(51) Int. Cl.
*C10G 69/04*    (2006.01)
*B01D 3/40*    (2006.01)
*B01J 19/24*    (2006.01)

(52) U.S. Cl.
CPC .............. *C10G 69/04* (2013.01); *B01D 3/40* (2013.01); *B01J 19/245* (2013.01);
(Continued)

(58) Field of Classification Search
CPC .............. C10G 69/04; C10G 2300/202; C10G 2300/301; C10G 2300/305; C10G 2300/307; C10G 2400/02; C10G 2400/04; C10G 2400/20; C10G 2400/22; C10G 2400/30; C10G 45/32; C10G 51/06; C10G 65/12; C10G 65/14; C10G 69/14;
(Continued)

(56) References Cited

U.S. PATENT DOCUMENTS

| 5,685,972 A | 11/1997 | Timken et al. |
| 6,410,813 B1 | 6/2002 | Dath et al. |

(Continued)

FOREIGN PATENT DOCUMENTS

| CN | 101531558 A | 9/2009 |
| EP | 3017026 B1 | 2/2019 |

(Continued)

OTHER PUBLICATIONS

India Examination Report, dated Nov. 17, 2021, for India Patent Application No. 202021017031 filed Apr. 21, 2020.
(Continued)

*Primary Examiner* — Thuan D Dang
(74) *Attorney, Agent, or Firm* — Workman Nydegger (57) ABSTRACT

The invention relates to a process configuration for production of light olefins and aromatics from residual hydrocarbon streams. In this configuration a high severity catalytic cracking process is employed for producing higher yields of lighter olefins and various boiling fractions. C4 stream separated from gaseous product is subjected to metathesis and aromatized to form mono aromatics.

8 Claims, 2 Drawing Sheets

(52) U.S. Cl.
CPC . *B01J 2219/0004* (2013.01); *C10G 2300/202* (2013.01); *C10G 2300/301* (2013.01); *C10G 2300/305* (2013.01); *C10G 2300/307* (2013.01); *C10G 2400/02* (2013.01); *C10G 2400/04* (2013.01); *C10G 2400/20* (2013.01); *C10G 2400/22* (2013.01); *C10G 2400/30* (2013.01)

(58) Field of Classification Search
CPC ...... C10G 2400/06; C10G 11/18; C10G 7/08; C10G 35/04; B01D 3/40; B01J 19/245; B01J 2219/0004; Y02P 20/52; C07C 5/393; C07C 6/04
See application file for complete search history.

(56) References Cited

U.S. PATENT DOCUMENTS

| | | |
|---|---|---|
| 9,434,894 B2 | 9/2016 | Mehlberg et al. |
| 9,644,155 B2 | 5/2017 | Butley et al. |
| 9,650,579 B2 | 5/2017 | Fanget et al. |
| 9,856,425 B2 | 1/2018 | Ward et al. |
| 10,717,941 B2 | 7/2020 | Al-Ghamdi et al. |

FOREIGN PATENT DOCUMENTS

| | | |
|---|---|---|
| KR | 20190087459 A | 7/2019 |
| RU | 2615160 C2 | 4/2017 |
| RU | 2733842 C2 | 10/2020 |
| RU | 2733847 C2 | 10/2020 |
| WO | 2018/048611 A1 | 3/2018 |
| WO | 2015128019 A1 | 5/2018 |
| WO | 2018094343 A1 | 5/2018 |
| WO | 2018094351 A1 | 5/2018 |

OTHER PUBLICATIONS

Extended European Search Report, dated Sep. 8, 2021, for European patent application No. 21168136 filed Apr. 21, 2020.

PROCESS CONFIGURATION FOR PRODUCTION OF PETROCHEMICAL FEED-STOCKS

FIELD OF THE INVENTION

The present invention relates to a process configuration for production of light olefins and aromatics from residual hydrocarbon streams.

BACKGROUND OF THE INVENTION

Refining industry is a capital-intensive industry. Refiners face major challenges due to fluctuations in global prices of crude oil and products which affect the gross refinery margin. Stringent emission norms for automotive fuel increase the hydrogen requirements for hydrotreatment of high sulfur fuels. This increases the dependency for import of natural gas. Environmental concerns also lead to development of renewable products which will cause a decline in demand for refinery products. Also, due to the advent of electric vehicles, there might be a decrease in demand of distillate fuels. Therefore, there is a need to convert the distillate fuels to more valuable alternate finished products. The importance and demand for petrochemicals are growing day by day. The olefins and aromatics are the basic building blocks for the petrochemical units. These are produced by cracking feedstocks such as light gases and middle distillates. Olefinic compounds such as ethylene, propylene, and aromatic compounds such as benzene, toluene, xylene, and alkyl substituted mono aromatics are highly useful in petrochemical industry. The present invention produces mainly olefins, mono aromatics, and high valuable streams from high severity FCC unit. In this invention all the product streams such as naphtha, light cycle oil, and clarified oil from high severity FCC unit are subjected to various conversion processes for production of light olefins, mono aromatics and high quality distillate streams. The present configuration maximizes petrochemical feedstocks in the light of declining demand of transportation fuels.

U.S. Pat. No. 9,434,894 describes a process for processing hydrocarbons including fractionating a hydrocarbon stream to form at least two fractions. The first fraction is reformed to form a reformate stream, and the reformate stream is introduced into an aromatics processing zone to produce aromatic products. At least a portion of the second fraction is cracked in a fluid catalytic cracking unit. A selectively hydrogenated light naphtha stream is formed by separating the cracked hydrocarbon stream into at least two streams and selectively hydrogenating the light naphtha stream, or selectively hydrogenating the cracked hydrocarbon stream and separating the hydrogenated cracked hydrocarbon stream into at least two streams. Aromatics are extracted from the selectively hydrogenated light naphtha stream forming an extract stream and a raffinate stream. The extract stream is hydrotreated, sent to the aromatics processing zone to produce additional aromatic products. It also talks about aromatics extractive distillation and using the olefinic FCC raffinate stream in gasoline blending. The main shortcoming of this invention is the process employed to produce aromatics from the crude distillation unit utilizing only the straight run naphtha and naphtha stream from FCC. In the present invention, the complete products from FCC main fractionator are utilized for production of light olefins and aromatics as petrochemical feedstocks.

U.S. Pat. No. 5,685,972 relates to an integrated process of hydro treatment and catalytic treatment where in the naphtha is hydrotreated and treated on acidic catalyst to produce BTX and low sulfur gasoline. The main disadvantage of this invention is that, only naphtha produced from FCC is used for production of BTX. In the current invention, the process flow configuration gives an advantage of producing higher yield of light olefins and aromatics along with high quality distillate fuels.

U.S. Pat. No. 9,650,579B2 refers to FCC units processing heavy feedstocks enriched with hydrogen, such as for example a highly hydrotreated VGO, or the unconverted part at the end of hydrocracking this same type of VGO feedstock, feedstocks which have the characteristic of cracking to light olefins such as ethylene and propylene. The integration of an FCC with an aromatic complex allows the recovery by the aromatic complex of the BTX formed in the FCC, and the recovery by the FCC from the flow at the bottom of the column, of heavy aromatics from the aromatic complex. The disadvantage of the process of U.S. Pat. No. 9,650,579B2 is that there is a requirement for an aromatic complex for integration for the production of light olefins whereas the process flow configuration of the present invention produces higher yields of light olefins and aromatics along with high quality distillate fuels due to various processes being applied on the resultant streams from the high severity FCC unit.

U.S. Pat. No. 9,644,155 provides an integrated process for production of ultra-low sulfur products of high octane gasoline, high aromatic naphtha and high Cetane Diesel by subjecting high aromatic middle distillate range streams from any cracker units such as Light Cycle Oil (LCO) stream of FCC units to hydrotreating for removal of heteroatoms such as sulfur and nitrogen. The effluent from hydrotreating is subjected to hydrocracking at same pressure of hydrotreating step above for selective opening of saturated ring of multi-ring aromatics. The effluent from hydrocracking is separated into CUT1 and CUT 2 in which the monoaromatics and alkylated monoaromatics are concentrated and CUT3 in which concentration of saturates significantly increased. The CUT-3 is selectively oxidized to produce a diesel product with more enhanced Cetane. The feed used in U.S. Pat. No. 9,644,155 is a low boiling point stream, whereas the process of the present invention converts a high boiling stream into light olefins and aromatic feedstocks.

WO2018048611A1 relates to systems and methods for crude oil separation and upgrading, which include the ability to reduce aromatic complex bottoms content in gasoline and higher-quality aromatic compounds. In some embodiments, aromatic complex bottoms are recycled for further processing. In some embodiments, aromatic complex bottoms are separated for further processing. This reference provides diesel with good cetane number and gasoline with optimum octane number by using hydrocracking, aromatization and hydrotreatment. Crude is distilled and only naphtha stream is utilized to produce aromatic compounds in WO2018048611A1, whereas in the present invention all the streams from the high severity FCC unit are utilized to produce light olefins and aromatic feedstocks.

U.S. Ser. No. 10/717,941 discloses a process an integrated process for converting crude oil to petrochemical products including olefins and aromatics, and fuel products, includes mixed feed steam cracking and fluid catalytic cracking. It also provides teachings regarding use of metathesis reaction for producing additional propylene, use of delayed coker for thermal coking to produce petroleum coke and also hydrocracking reactions. In U.S. Ser. No. 10/717,941, crude is distilled and a cascade of hydroprocessing units are used for conversion of vacuum gas oil streams, whereas in the present invention all the streams from the high severity FCC unit are utilized to produce light olefins and aromatic rich feedstocks. The quality of liquid distillates produced in this invention is of high quality in terms of octane and cetane numbers. This invention partially caters to the need of supply of fuels in conventional refinery configuration along with production of petrochemicals.

SUMMARY OF THE INVENTION

Aromatics and alkyl substituted aromatics (mainly BTX) are used as the feedstocks for petrochemicals industry. These compounds are the basic building blocks for the production of polyester, purified terephthalic acid, phthalic anhydride, styrene, polystyrene, specialty solvents and numerous other components. Conventionally these compounds are obtained from petroleum crude refining industry. The various processes such as catalytic cracking, catalytic reforming of some of the refinery streams produce these compounds along with the other products which are recovered by separation process.

The continually increasing cost of energy in refining and more stringent environmental norms on transportation fuels (mainly on gasoline and diesel) are making the impact on profit margin of petroleum refinery. For improving the profit margin, it is necessary to upgrade the low value streams such as naphtha and residual streams by employing cost effective technologies to more valuable products as feedstocks to chemical/petrochemical industries. In the current invention, new process configuration and unit integration are employed in synergistic sequence for increasing the yields of light olefins and mono aromatics as compared to the conventional refinery configuration.

In one aspect, the present invention relates to an integrated process for producing light olefins and aromatics from residual hydrocarbon streams comprising:

a) subjecting a residual hydrocarbon stream (10) to catalytic cracking to produce a catalytically cracked effluent, wherein the catalytically cracked effluent is fractionated into a C3-C4 stream (12), light cracked naphtha (13), heavy cracked naphtha (14), light cycle oil (15), and clarified oil (16), b) separating the C3-C4 stream (12) into a propylene containing stream (18) and a butylene and pentene containing stream (19), c) subjecting the butylene and pentene containing stream (19) to metathesis and separation to produce propylene (21) and hexenes (22), wherein hexenes (22) is aromatized to produce benzene and alkyl substituted benzenes (24) and an unconverted stream (25), d) selectively hydrogenating the light cracked naphtha (13) to produce a selectively hydrogenated stream comprising olefins and saturates (27), e) subjecting the selectively hydrogenated stream (27) to extractive distillation using a solvent to form an extract stream (30) containing aromatics along with sulfur compounds and a raffinate stream (29) containing olefins and hydrotreating the extract stream (30) to obtain stream (32), f) combining the heavy cracked naphtha (14) along with liquid hydrocarbon streams boiling in the range of C5-210° C. (52) from a delayed coker unit (50) in a circulating fluidized bed reactor for fractionation into dry gas (34), C3-C4 stream (35), liquid hydrocarbon streams boiling in the range of C5-70° C. (36), 70-170° C. (37) and 170° C.+ (38), g) hydrotreating the light cycle oil (15) to produce an intermediate stream (40), h) hydrocracking the intermediate stream (40) to produce a hydrocracked stream (42) which is fractionated into additional products, i) hydrotreating the clarified oil (16) to produce a hydrotreated stream (49), wherein the hydrotreated stream (49) is fed to a delayed coker unit (50) to produce lighter products and needle coke (54), wherein the lighter products are gases (51), liquid hydrocarbon streams boiling in the range of C5-210° C. (52), and diesel (53), wherein the process yields light olefins in a range of 11-15 weight % and aromatics in a range of 15-21 weight %, and wherein in the weight % is with reference to the residual hydrocarbon stream.

In another aspect, the stream (25) rich in higher olefins with good octane number and stream (38) are routed to gasoline pool (55).

In a further aspect, the present invention provides that the hydrotreating of step g) removes hetero atoms and selectively saturates the poly aromatics to di aromatics and di aromatics to mono aromatics.

In yet another aspect, the stream (47) and stream (53) are blended into a diesel pool (56).

In a preferred aspect, the stream (47) has a cetane number in a range of 30-42 and stream (53) has a cetane number in a range of 22-30.

In yet another preferred aspect, the stream (25) has an octane number in a range of 90-93 and stream (38) has an octane number in a range of 90-95.

In one aspect, stream (42) is fractionated into dry gas (43), C3-C4 stream (44), liquid hydrocarbon streams boiling in the range of C5-70° C. (45), 70-170° C. (46) rich in mono aromatics and alkyl substituted mono aromatics and 200° C.+ (47).

In an aspect of the present invention, the general selective solvents or a combination of solvents are used for extractive distillation. The solvents are ethylene glycol, sulfolane, dimethylsulfoxide, etc.

In a preferred aspect, the present invention relates to a system for producing light olefins and aromatics from residual hydrocarbon streams, comprising:

(a) a high severity catalytic cracking unit (11) for cracking C3-C4 stream (12) and fractionating the catalytically cracked effluent, wherein the high severity catalytic cracking unit is in communication with a propylene splitter unit (17), a metathesis reactor and separation unit (20), hydrotreater (48), hydrotreater (39), and a circulating fluidized bed reactor (33), (b) a propylene splitter unit (17)

(c) a metathesis reactor and separation unit (20) to produce propylene (21) and hexenes (22) by metathesis, (d) an aromatizing reactor unit (23) to aromatize hexenes (22), (e) a selective hydrogenation unit (26) to convert all the di-olefins responsible for gum formation and fouling present in light cracked naphtha (13) to olefins and saturates forming part of a selectively hydrogenated stream (27), (f) an extractive distillation column (28) for producing an extract stream (30) and a raffinate stream (29) from the selectively hydrogenated stream (27), (g) hydrotreaters (31), (39) and (48), wherein hydrotreater (31) is downstream of an extractive distillation column (28) and hydrotreaters (39) and (48) are downstream of the high severity catalytic cracking unit, and wherein hydrotreater (39) removes hetero atoms and selectively saturates poly aromatics to di aromatics and di aromatics to mono aromatics from light cycle oil (15) and hydrotreater (48) removes sulfur and metals from clarified oil (16) to make a desirable feed stock for producing needle coke, (h) a circulating fluidized bed reactor (33) for treating the combined stream of heavy cracked naphtha (14) and liquid hydrocarbon streams boiling in the range of C5-210° C. (52) and fractionating the reactor effluent, (i) a mild hydrocracking unit (41) for selective ring opening of di or poly aromatics in intermediate stream (40) to produce a hydrocracked stream (42), (j) a delayed coker unit (50) for thermally cracking stream (49) to produce and fractionate lighter products and needle coke (54).

In another aspect, the high severity catalytic cracking unit (11) operates at a pressure in a range of 1.5 to 2 $kg/cm^2$ (g) and temperature in a range of 540 to 600° C.

In yet another aspect, the hydrotreaters (31), (39) and (48) operate at a pressure in a range of 30 to 120 $kg/cm^2$ (g) and temperature in a range of 300 to 400° C.

In a further aspect, the hydrocracking unit (41) operates at a pressure in a range of 80 to 130 $kg/cm^2$ (g) and temperature in a range of 250 to 420° C.

Objectives of the Invention:

A primary objective of the invention is to provide a process configuration for production of light olefins and aromatics from residual hydrocarbon streams.

A further objective of the present invention is to produce light olefins and monoaromatics from high boiling hydrocarbon stream involving high severity catalytic cracking process followed by various catalytic and thermal refining processes.

Another object of this invention is to produce higher yields of lighter olefins and various boiling fractions by employing high severity catalytic cracking process.

Yet another objective of the invention is to subject the C4 stream separated from gaseous product to metathesis and aromatization to form monoaromatics.

DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps of the process, features of the product, referred to or indicated in this specification, individually or collectively, and any and all combinations of any or more of such steps or features. The present disclosure is not to be limited in scope by the specific embodiments described herein, which are intended for the purposes of exemplification only. Functionally-equivalent products and methods are clearly within the scope of the disclosure, as described herein.

In the conventional FCC (FIG. 1) gas con section, FCC reactor effluent (1) is fractionated into different cuts in a FCC main fractionator (2). The hot vapors from the reactor enter the bottom section of the column. These vapors are fractionated to produce the following products: DG and LPG (3), Light naphtha to treatment and blending to gasoline pool (4), Heavy naphtha to DHDT/HGU unit (5), Light cycle oil to DHDT (6), Clarified oil to Fuel oil (7). These streams undergo treatment before being blended into the finished products.

Figure 1:
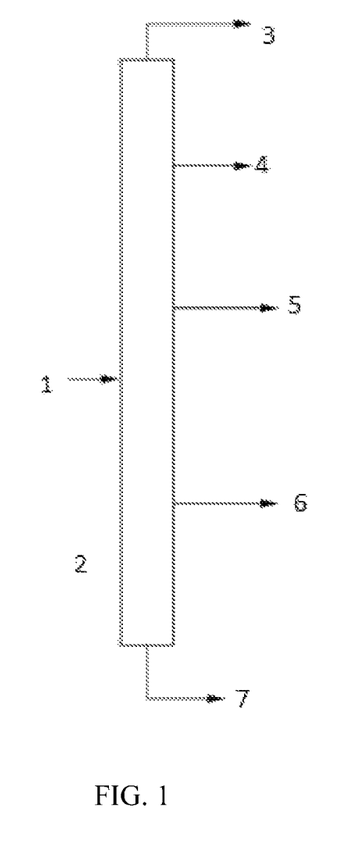
FIG. 1 illustrates conventional FCC main fractionator and utilization of streams.

According to the main feature, in the present invention, these streams are further subjected to different types of new catalytic processes which convert them further into more additional valuable products such as light olefins, BTX, high octane gasoline and high cetane diesel along with premium grade petroleum coke.

In one embodiment, the present invention provides an integrated process for producing light olefins and aromatics from residual hydrocarbon streams comprising:

a) subjecting a residual hydrocarbon stream (10) to catalytic cracking to produce a catalytically cracked effluent, wherein the catalytically cracked effluent is fractionated into a C3-C4 stream (12), light cracked naphtha (13), heavy cracked naphtha (14), light cycle oil (15), and clarified oil (16), b) separating the C3-C4 stream (12) into a propylene containing stream (18) and a butylene and pentene containing stream (19), c) subjecting the butylene and pentene containing stream (19) to metathesis and separation to produce propylene (21) and hexenes (22), wherein hexenes (22) is aromatized to produce benzene and alkyl substituted benzenes (24) and an unconverted stream (25), d) selectively hydrogenating the light cracked naphtha (13) to produce a selectively hydrogenated stream comprising olefins and saturates (27), e) subjecting the selectively hydrogenated stream (27) to extractive distillation using a solvent to form an extract stream (30) containing aromatics along with sulfur compounds and a raffinate stream (29) containing olefins and hydrotreating the extract stream (30) to obtain stream (32), f) combining the heavy cracked naphtha (14) along with liquid hydrocarbon streams boiling in the range of C5-210° C. (52) from a delayed coker unit (50) in a circulating fluidized bed reactor for fractionation into dry gas (34), C3-C4 stream (35), liquid hydrocarbon streams boiling in the range of C5-70° C. (36), 70-170° C. (37) and 170° C.+ (38), g) hydrotreating the light cycle oil (15) to produce an intermediate stream (40), h) hydrocracking the intermediate stream (40) to produce a hydrocracked stream (42) which is fractionated into additional products, i) hydrotreating the clarified oil (16) to produce a hydrotreated stream (49), wherein the hydrotreated stream (49) is fed to a delayed coker unit (50) to produce lighter products and needle coke (54), wherein the lighter products are gases (51), liquid hydrocarbon streams boiling in the range of C5-210° C. (52), and diesel (53)

wherein the process yields light olefins in a range of 11-15 weight % and aromatics in a range of 21-30 weight % in stream (52)

wherein in the weight % is with reference to the residual hydrocarbon stream.

In another embodiment, the stream (25) rich in higher olefins with good octane number and stream (38) are routed to gasoline pool (55).

In a further embodiment, the present invention provides that the hydrotreating of step g) removes hetero atoms and selectively saturates the poly aromatics to di aromatics and di aromatics to mono aromatics.

In yet another embodiment, the stream (47) and stream (53) are blended into a diesel pool (56).

In a preferred embodiment, the stream (47) has a cetane number in a range of 30-42 and stream (53) has a cetane number in a range of 22-30.

In yet another preferred embodiment, the stream (25) has an octane number in a range of 90-93 and stream (38) has an octane number in a range of 90-95.

In one embodiment, stream (42) is fractionated into dry gas (43), C3-C4 stream (44), liquid hydrocarbon streams boiling in the range of C5-70° C. (45), 70-170° C. (46) rich in mono aromatics and alkyl substituted mono aromatics and 200° C.+ (47).

In an embodiment of the present invention, the general selective solvents such as ethylene glycol, sulfolane, dimethylsulfoxide, etc., or a combination of solvents are used for extractive distillation.

In a preferred embodiment, the present invention provides a system for producing light olefins and aromatics from residual hydrocarbon streams, comprising:

(a) a high severity catalytic cracking unit (11) for cracking C3-C4 stream (12) and fractionating the catalytically cracked effluent, wherein the high severity catalytic cracking unit is in communication with a propylene splitter unit (17), a metathesis reactor and separation unit (20), hydrotreater (48), hydrotreater (39), and a circulating fluidized bed reactor (33), (b) a propylene splitter unit (17)

(c) a metathesis reactor and separation unit (20) to produce propylene (21) and hexenes (22) by metathesis, (d) an aromatizing reactor unit (23) to aromatize hexenes (22), (e) a selective hydrogenation unit (26) to convert all the di-olefins responsible for gum formation and fouling present in light cracked naphtha (13) to olefins and saturates forming part of a selectively hydrogenated stream (27), (f) an extractive distillation column (28) for producing an extract stream (30) and a raffinate stream (29) from the selectively hydrogenated stream (27), (g) hydrotreaters (31), (39) and (48), wherein hydrotreater (31) is downstream of an extractive distillation column (28) and hydrotreaters (39) and (48) are downstream of the high severity catalytic cracking unit, and wherein hydrotreater (39) removes hetero atoms and selectively saturates poly aromatics to di aromatics and di aromatics to mono aromatics from light cycle oil (15) and hydrotreater (48) removes sulfur and metals from clarified oil (16) to make a desirable feed stock for producing needle coke, (h) a circulating fluidized bed reactor (33) for treating the combined stream of heavy cracked naphtha (14) and liquid hydrocarbon streams boiling in the range of C5-210° C. (52) and fractionating the reactor effluent, (i) a mild hydrocracking unit (41) for selective ring opening of di or poly aromatics in intermediate stream (40) to produce a hydrocracked stream (42), (j) a delayed coker unit (50) for thermally cracking stream (49) to produce and fractionate lighter products and needle coke (54).

In another embodiment, the high severity catalytic cracking unit (11) operates at a pressure in a range of 1.5 to 2 kg/cm$^2$ (g) and temperature in a range of 540 to 600° C.

In yet another embodiment, the hydrotreaters (31), (39) and (48) operate at a pressure in a range of 30 to 120 kg/cm$^2$ (g) and temperature in a range of 300 to 400° C.

In a further embodiment, the hydrocracking unit (41) operates at a pressure in a range of 80 to 130 kg/cm$^2$ (g) and temperature in a range of 250 to 420° C.

Description of Process Flow Scheme

Figure 2:
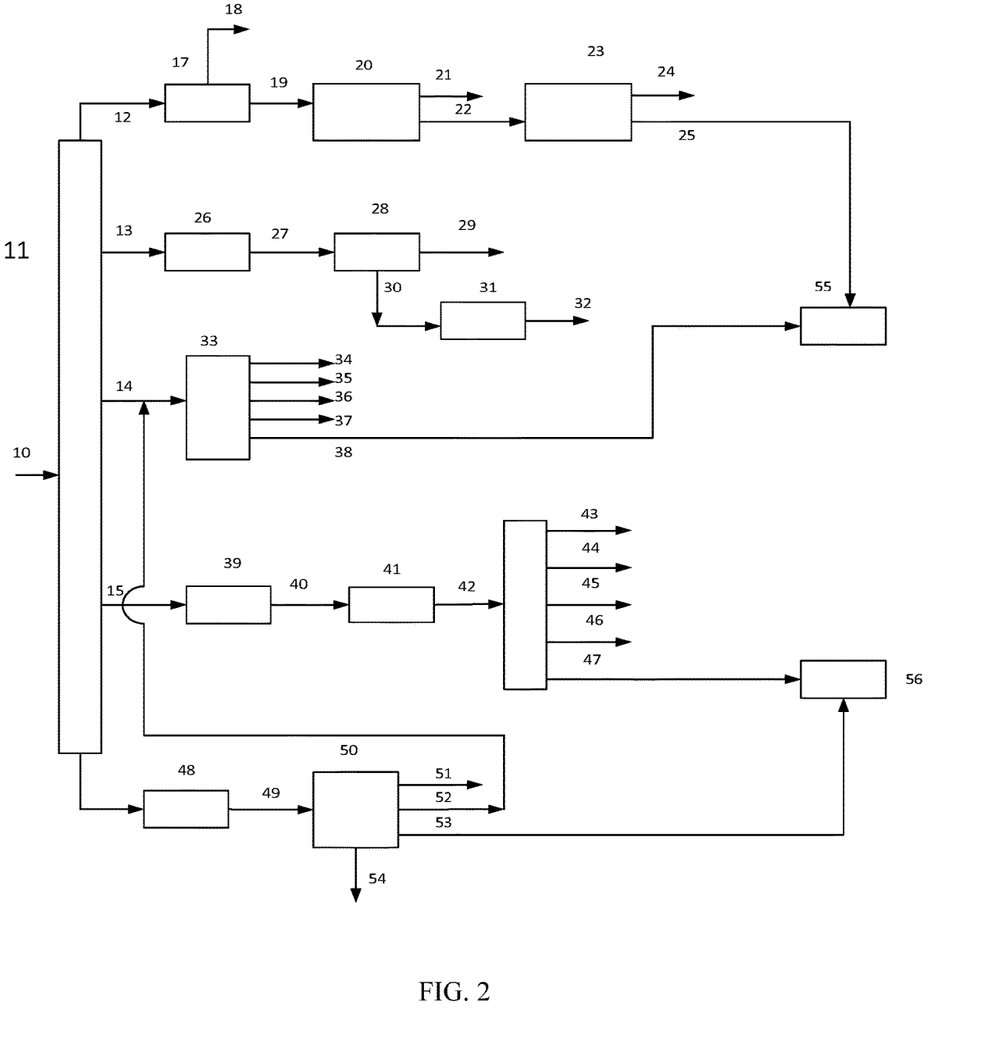
FIG. 2 illustrates process of the present invention.

As shown in FIG. 2, high severity catalytic cracking unit (11) is fed with residual hydrocarbon stream (10) and the reactor effluent is fractionated into various product streams such as C3-C4 stream (12), liquid hydrocarbon streams boiling in the range of C5-70° C. and 70-170° C. (13), 170-210° C. (14), 210-370° C. (15) and 370° C.+. The stream 12 sent to propylene splitter unit (17) where propylene is separated from stream 12 into stream 18 which contains 99.7 wt % C$_3$s and stream (19) containing mostly C$_4$ and C$_5$s. Stream (19) with 99.7% C4's is fed to a metathesis reactor and separation unit (20). Unit (20) produces propylene (21) and hexenes (22) by metathesis from stream (19) containing butenes and pentanes. Stream (22) is fed to aromatizing reactor unit (23) where the hexenes (22) along with higher olefins are aromatized to benzene and alkyl substituted benzenes (24). The unconverted stream (25) rich in higher olefins like hexenes, heptenes and octenes with good octane number will be routed to gasoline pool (55). The light naphtha stream (13) comprising 30 wt % olefins, 5 wt % di olefins and 40 wt % aromatics are fed to a selective hydrogenation unit (26). In this unit, all the di olefins which are the sources for gum formation and fouling are converted to olefins and saturates. The selectively hydrogenated stream (27) is sent to an extractive distillation column (28). The solvent extracts the aromatics along with sulfur compounds as stream (30) whereas olefins rich stream (29) is the raffinate in an extraction column operating at a temperature range of 30-180° C. After solvent recovery, stream (30) is hydrotreated and directed to an aromatics plant with 99% rich in aromatics. The stream (14) along with (52) is fed to (33) which is typically a circulating fluidized bed reactor. The reactor effluent is fractionated into various product streams such as dry gas (34), C3-C4 stream (35), liquid hydrocarbon streams boiling in the range of C5-70° C. (36), 70-170° C. (37) and 170° C.+ (38). The stream (15) is fed to a hydrotreater unit (39) to remove the hetero atoms such as sulfur and to selectively saturate the poly aromatics to di aromatics and di aromatics to mono aromatics. Effluent from unit (39), stream (40) is processed in mild hydrocracking unit (41) for selective ring opening of di/poly aromatics. Stream (42) is fractionated to various products such as dry gas (43), C3-C4 stream (44), liquid hydrocarbon streams boiling in the range of C5-70° C. (45), 70-170° C. (46) which is rich in mono aromatics and alkyl substituted mono aromatics and 200° C.+ (47) having a good cetane number of 42 which is blended into diesel pool (56). The stream (16) is subjected to hydrotreating in unit (48) to remove the sulfur and metals to make a desirable feed stock for producing needle coke. Stream (49) is fed to delayed coker unit (50) for thermally cracking the feedstock to produce lighter products along with needle coke (54). The lighter products are fractionated into various products such as gases (51), liquid hydrocarbon streams boiling in the range of C5-210° C. (52), and 210-370° C. (53) diesel stream which can be routed to diesel pool (56).

Technical Advantages of the Invention:

The present invention has the following advantage over the prior arts:

1. The present invention produces high amount of propylene and mono-aromatics from high boiling hydrocarbon streams.
2. The present invention also produces gasoline with high octane number and diesel with high cetane number which can be blended directly into its pools.
3. This invention further produces saturated LPG for use as fuel to automobiles and premium quality petroleum needle coke for manufacturing of electrodes in arc furnaces in the steel industry.

From the above process flow scheme, it can be seen that the process configuration of current invention converts the streams from high severity FCC unit into propylene, aromatics and octane rich gasoline, cetane rich diesel along with premium quality petroleum coke.

Examples

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods, the exemplary methods, devices, and materials are described herein. It is to be understood that this disclosure is not limited to particular methods, and experimental conditions described, as such methods and conditions may vary.

The yields of the processes are established in pilot plants experiments and simulation of the entire configuration is carried out in AspenHYSYS software. The typical yields of high severity FCC unit which is the starting unit in this configuration are shown in Table-1. Typical yields of conversion process units in the above configuration are shown in Table-2, 3, 4, respectively.

TABLE 1

True boiling point (TBP) yields of high severity catalytic cracking unit (11)

| Products | Wt % |
| --- | --- |
| Dry gas (w/o inert) | 10.91 |
| LPG | 44.15 |
| LCN (C5-70° C.) | 9.19 |
| MCN (70-170° C.) | 17.14 |
| HCN (170-210° C.) | 2.69 |
| LCO (210-340° C.) | 7.88 |
| CLO (340° C.+) | 2.24 |
| Coke | 5.8 |

TABLE 2

Yields of conversion unit-33

| Products | Wt % |
| --- | --- |
| Dry gas | 7.33 |
| LPG | 43.88 |
| Benzene rich cut (70-90° C.) | 5.80 |
| Benzene lean cut (C5-70° C. and 90-210° C.) | 40.89 |
| Coke | 2.10 |

TABLE 3

Yields of conversion unit-41

| Products | Wt % |
| --- | --- |
| Dry gas | 1.5 |
| LPG | 8.0 |

TABLE 3-continued

Yields of conversion unit-41

| Products | Wt % |
| --- | --- |
| Light Naphtha (C5-100° C.) | 15.0 |
| Heavy Naphtha (100-200° C.) | 55.0 |
| Diesel (200+° C.) | 20.5 |

TABLE 4

Yields of conversion unit-50

| Products | Wt % |
| --- | --- |
| Dry gas | 8.7 |
| LPG | 2.6 |
| Naphtha | 5.1 |
| Gas oil | 33.0 |
| Needle coke | 50.6 |

The comparison of typical yields obtained from Fig-1 and Fig-2 process are given in Table 5.

TABLE 5

| Product Yields, wt % | FIG. 1 | FIG. 2 |
| --- | --- | --- |
| Dry Gas | 2.48 | 7.02 |
| LPG | 24.53 | 42.0 |
| Propylene | 9.77 | 17.4 |
| Gasoline (C5-210) | 50.98 | 35.19 |
| LCO (210-340) | 9.73 | 7.59 |
| CLO (340+) | 7.97 | 2.16 |
| Coke | 4.31 | 6.0 |

Table 5 shows that further processing of the stream obtained from unit no (11) by using the present configuration as described in the present invention produces light olefins, mono aromatics, gasoline with octane number in the range of 90-95, diesel with cetane number in the range of 30-42 along with the needle coke. The process leads to an increase in the yield of dry gas, LPG, propylene and coke and reduction in the yields of gasoline, light cycle oil and clarified oil.

Light cycle oil (15) undergoes conversion in unit (39) to an intermediate (40) and the change in quality in the typical temperature range of 300 to 400° C. and pressure range of 30 to 120 kg/cm' (g) is given in Table 6. Table 6 demonstrates that hydrotreatment of the light cycle oil (15) reduces the sulfur content, increases the content of saturates and mono aromatics, while reducing the content of di aromatics and poly aromatics.

TABLE 6

|  | Stream No-15 | Stream No-40 |
| --- | --- | --- |
| Sulfur, ppm | 9500 | 6.2 |
| Saturates, wt % | 24 | 34 |
| Mono Aromatics | 39.6 | 51.5 |
| Di Aromatics | 36.1 | 14.4 |
| Poly Aromatics | 0.3 | 0.1 |

The typical yields of the unit (39) in the typical temperature range of 300 to 400° C. and pressure range of 30 to 120 kg/cm$^2$ (g) is given in Table 7.

TABLE 7

| Product Yields | Wt % |
|---|---|
| H$_2$S | 1.54 |
| NH$_3$ | 0.04 |
| Fuel gas | 0.85 |
| Naphtha | 1.3 |
| Diesel | 98.7 |

The reactor temperature and pressure ranges are very critical in achieving the desired result of decreasing sulfur, di aromatics and poly aromatics content in the feed which forms the desired feed to the hydrocracking unit (41). The yield and product quality from the hydrocracking unit (41) depends on the quality of intermediate stream (40). However, if the temperature in the hydrotreatment unit (39) is decreased to 290° C. and the pressure is 35 kg/cm$^2$, the conversion of di aromatics to mono aromatics, poly aromatics to di aromatics and sulfur compounds to H$_2$S decreases. The composition of intermediate stream (40) at 290° C. and 25 kg/cm$^2$ is given in Table 8.

TABLE 8

|  | Stream No-15 | Stream No-40 |
|---|---|---|
| Sulfur, ppm | 9500 | 3610 |
| Saturates, wt % | 24 | 27.0 |
| Mono Aromatics | 39.6 | 46.8 |
| Di Aromatics | 36.1 | 26.0 |
| Poly Aromatics | 0.3 | 0.19 |

When the temperature in unit (39) is decreased to 290° C. and pressure is reduced to 25 kg/cm$^2$ conversion of di aromatics to mono aromatics, poly aromatics to di aromatics and sulfur compounds to H$_2$S decreases.

TABLE 9

| Product Yields | Wt % |
|---|---|
| H$_2$S | 1.2 |
| NH$_3$ | 0.034 |
| Fuel gas | 0.662 |
| Naphtha | 1.20 |
| Diesel | 99.212 |

Similarly, when the temperature in unit (39) is increased to 400° C. and pressure is increased to 125 kg/cm$^2$ (g), desired yield of the products is not obtained.

TABLE 10

| Product Yields | Wt % |
|---|---|
| H$_2$S | 1.66 |
| NH$_3$ | 0.041 |
| Fuel gas | 0.98 |
| Naphtha | 1.7 |
| Diesel | 98.34 |

Similarly, the conversion of sulfur compounds to H$_2$S decreases from 99% to around 60% below pressure of 30 kg/cm$^2$ (g) and below temperature of 300° C. in hydrotreatment unit (31) and hydrotreatment unit (48).

If the temperature and pressure in a high severity catalytic cracking unit (11) are varied to 520° C. and 1.4 kg/cm$^2$ (g) respectively, the yield of light cycle oil and clarified oil increases, while lower yields of dry gas and LPG are obtained.

TABLE 11

| Product Yields | Wt % |
|---|---|
| Dry Gas | 3.75 |
| LPG | 32.53 |
| LCN (C5-70) | 15.50 |
| MCN (70-170) | 18.52 |
| HCN (170-210) | 1.38 |
| LCO (210-340) | 16.79 |
| CLO (340+) | 6.34 |
| Coke | 5.2 |

If the temperature and pressure in a high severity catalytic cracking unit (11) are varied to 600° C. and 1.4 kg/cm$^2$ (g) respectively, the yields of LCN, MCN, HCN and CLO clarified oil decreases while higher yields of dry gas and LPG are obtained as shown in Table-12.

TABLE 12

| Product Yields | Wt % |
|---|---|
| Dry Gas | 12.68 |
| LPG | 45.88 |
| LCN (C5-70) | 8.57 |
| MCN (70-170) | 15.10 |
| HCN (170-210) | 2.34 |
| LCO (210-340) | 7.51 |
| CLO (340+) | 2.21 |
| Coke | 5.72 |

The typical yields of the unit (41) at temperature of 70° C. and 240 kg/cm$^2$ (g) are given in Table-13.

TABLE 13

| Products | Wt % |
|---|---|
| Dry gas | 1.1 |
| LPG | 5.0 |
| Light Naphtha (C5-100° C.) | 8.0 |
| Heavy Naphtha (100-200° C.) | 47.0 |
| Diesel (200+° C.) | 38.9 |

The typical yields of the unit (41) at temperature of 135° C. and 425 kg/cm$^2$ (g) are given in Table-14.

TABLE 14

| Products | Wt % |
|---|---|
| Dry gas | 2.2 |
| LPG | 10.5 |
| Light Naphtha (C5-100° C.) | 24.0 |
| Heavy Naphtha (100-200° C.) | 52.0 |
| Diesel (200+° C.) | 11.3 |

On increasing the temperature and pressure beyond the ranges the yield and quality of heavy naphtha cut (100-200° C.) which is the good petrochemical feed stock decreases.

What is claimed is:

1. An integrated process for producing light olefins and aromatics from residual hydrocarbon streams, the process comprising:
   a) subjecting the residual hydrocarbon streams to catalytic cracking to produce a catalytically cracked effluent, wherein the catalytically cracked effluent is fractionated into a C3-C4 stream, light cracked naphtha, heavy cracked naphtha, light cycle oil, and clarified oil;
   b) separating the C3-C4 stream into a propylene containing stream and a butylene and pentene containing stream;

c) subjecting the butylene and pentene containing stream to metathesis and to a separation to produce propylene and hexenes, wherein the hexenes is aromatized to produce benzene and alkyl substituted benzenes and an unconverted stream;
d) selectively hydrogenating the light cracked naphtha to produce a selectively hydrogenated stream comprising olefins and saturates;
e) subjecting the selectively hydrogenated stream to extractive distillation using a solvent to form an extract stream containing aromatics along with sulfur compounds and a raffinate stream containing olefins and hydrotreating the extract stream to obtain a hydrotreated extract stream;
f) combining the heavy cracked naphtha along with liquid hydrocarbon streams boiling in the range of C5-210° C. from a delayed coker unit in a circulating fluidized bed reactor from step (i) for fractionation into a dry gas, a C3-C4 stream, a C5-70° C. stream, a 70-170° C. stream, a 170° C.+ stream, and a 200° C.+ stream;
g) hydrotreating the light cycle oil to produce an intermediate stream, wherein the intermediate stream comprises di aromatics or poly aromatics;
h) hydrocracking the intermediate stream to produce a hydrocracked stream, and fractionating the hydrocracked stream into additional products; and
i) hydrotreating the clarified oil to produce a hydrotreated stream, wherein hydrotreated stream is fed to the delayed coker unit to produce lighter products and needle coke, wherein the lighter products are gases, liquid hydrocarbon streams boiling in a range of C5-210° C., and diesel;

wherein the process yields light olefins in a range of 11-15 weight % and aromatics in a range of 15-21 weight %, and wherein in the weight % is with reference to the residual hydrocarbon stream streams.

2. The process as claimed in claim 1, wherein the unconverted stream, rich in higher olefins with a good octane number and the 170° C.+ stream are routed to a gasoline pool.

3. The process as claimed in claim 1, wherein the hydrotreating of step g) removes hetero atoms and selectively saturates the poly aromatics to di aromatics and the di aromatics to mono aromatics.

4. The process as claimed in claim 1, wherein the 200° C.+ stream and the diesel stream are blended into a diesel pool.

5. The process as claimed in claim 1, wherein the 200° C.+ stream has a cetane number in a range of 30-42 and the diesel stream has a cetane number in a range of 22-30.

6. The process as claimed in claim 1, wherein the unconverted stream has an octane number in a range of 90-93 and the 170° C.+ stream has an octane number in a range of 90-95.

7. The process as claimed in claim 1, wherein the hydrocracked stream is fractionated into dry gas, C3-C4 stream, liquid hydrocarbon streams boiling in a range of C5-70° C., 70-170° C. rich in mono aromatics and alkyl substituted mono aromatics and 200° C.+.

8. The process as claimed in claim 1, wherein the solvent used for the extractive distillation is general selective solvents or a combination of solvents for aromatics extraction.

* * * * *